United States Patent [19]

Bolz et al.

[11] 4,338,024

[45] Jul. 6, 1982

[54] FLOW ANALYZER AND SYSTEM FOR ANALYSIS OF FLUIDS WITH PARTICLES

[75] Inventors: Gunner Bolz, Del Mar; Sherman E. DeForest, Encinitas, both of Calif.

[73] Assignee: International Remote Imaging Systems, Inc., Chatsworth, Calif.

[21] Appl. No.: 146,064

[22] Filed: May 2, 1980

[51] Int. Cl.³ .................... G01N 33/48; G01N 21/05
[52] U.S. Cl. .................... 356/23; 340/146.3 CA; 356/39; 356/246
[58] Field of Search ............ 356/23, 39, 246; 250/461 B; 350/95; 235/92 PC; 340/146.3 CA

[56] References Cited

U.S. PATENT DOCUMENTS

| | | | |
|---|---|---|---|
| 2,480,312 | 8/1949 | Wolf | 235/92 PC |
| 2,791,150 | 5/1957 | Stevens | 235/92 PC |
| 3,390,229 | 6/1968 | Williams | 356/23 X |
| 3,560,754 | 2/1971 | Kamentsky | 250/218 |
| 3,819,270 | 6/1974 | Hirschfeld | 356/39 |
| 3,976,862 | 8/1976 | Curbelo | 235/151.34 |
| 4,075,462 | 2/1978 | Rowe | 235/92 PC |
| 4,097,845 | 6/1978 | Bacus | 356/39 X |
| 4,175,860 | 11/1979 | Bacus | 356/39 |
| 4,199,748 | 4/1980 | Bacus | 340/146.3 CA |

OTHER PUBLICATIONS

Edited by Melamed, et al.; *Flow Cytometry and Sorting*, 1979.

*Primary Examiner*—Vincent P. McGraw
*Attorney, Agent, or Firm*—Limbach, Limbach & Sutton

[57] ABSTRACT

The method and apparatus for analyzing particles and particularly blood cells by conveying the particles along a broad shallow path where the path is magnified and converted into a series of still frame images with multiple particles in individual images. The still frame images are manipulated and combined as digital images to generate measures of the blood cells in the overall fluid sample giving different selected measures, such as, particle count, particle count of different kinds of cells, cell area, and cell count of different predetermined categories of cell type.

16 Claims, 4 Drawing Figures

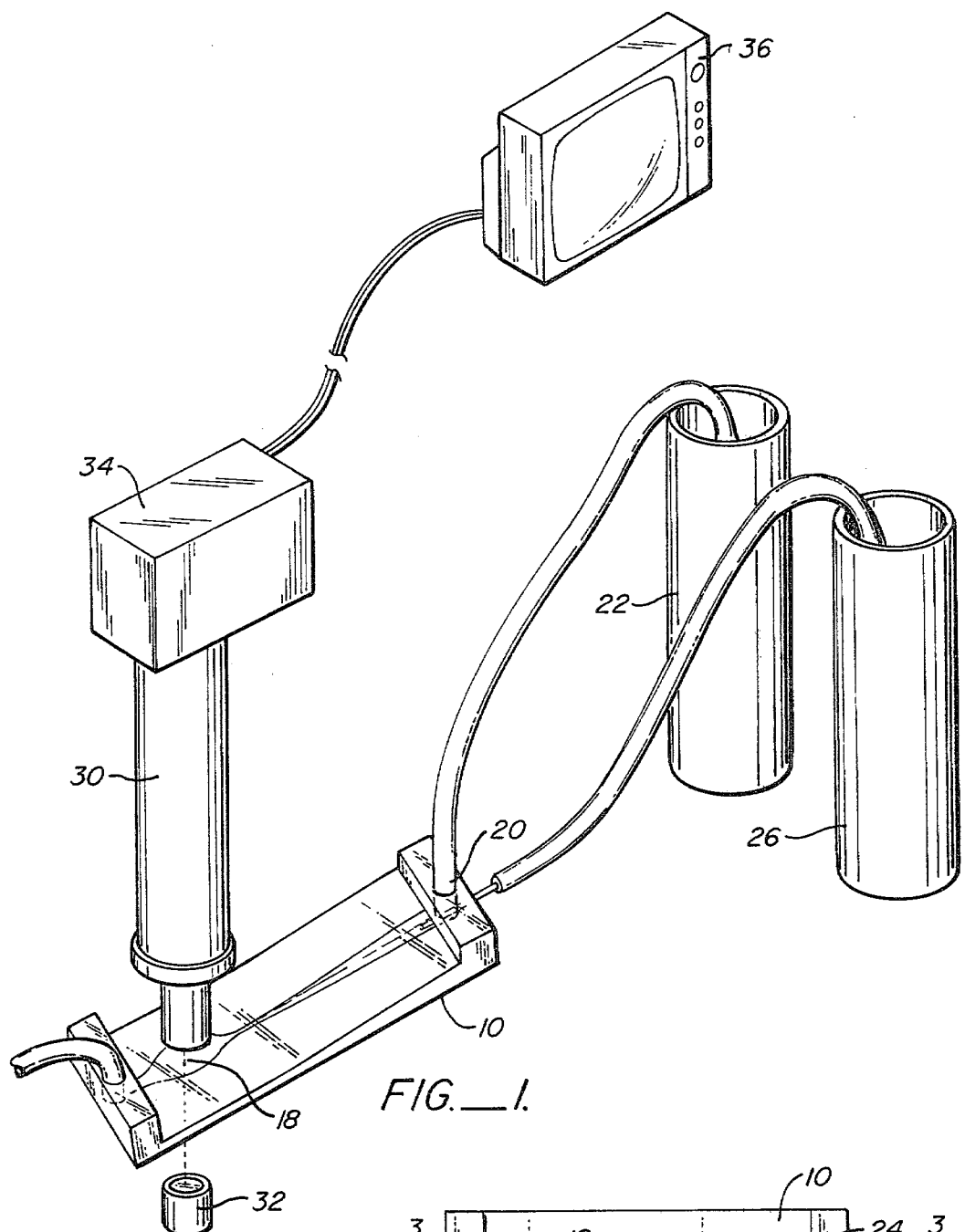
FIG._1.
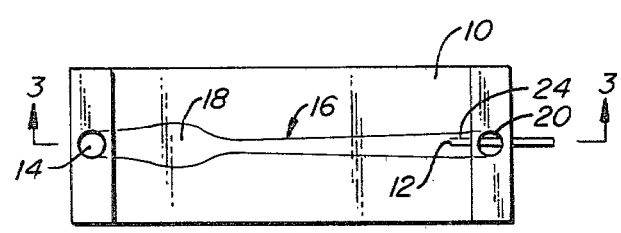
FIG._2.
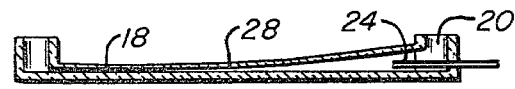
FIG._3.

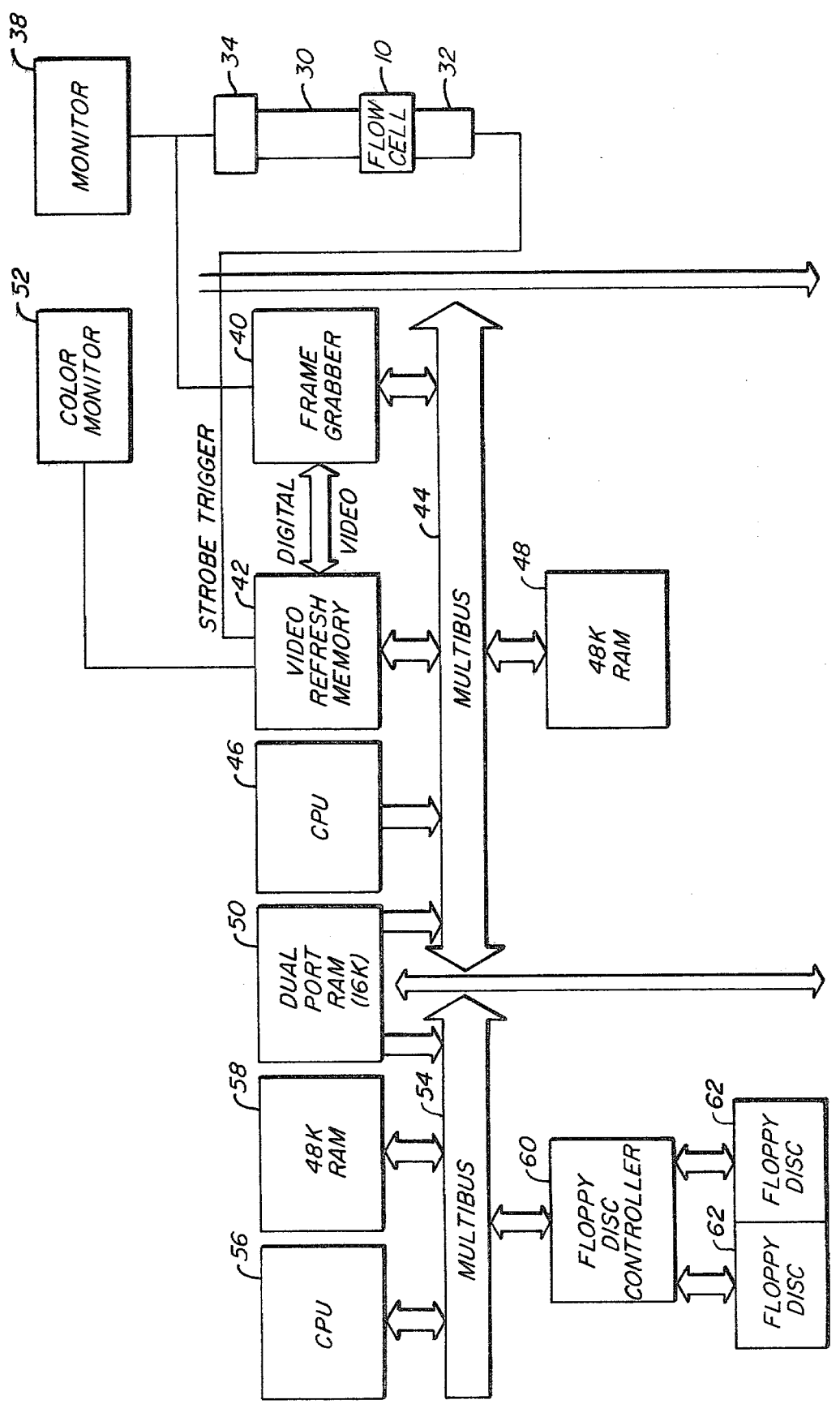
FIG._4.

FLOW ANALYZER AND SYSTEM FOR ANALYSIS OF FLUIDS WITH PARTICLES

BACKGROUND OF INVENTION

Substantial advances have been made in automating the job of counting blood cells in a serum sample. The most well-known instrument for performing blood counts is the so-called Coulter counter in which blood cells are passed in single file through an orifice and detected and counted by the manner in which they change the electric properties at the orifice. Up until the present time, however, there has been no automated equipment available for analyzing and evaluating the multiple cells, such as, normal cells, target cells, sickle cells, etc. which may be found in a flowing stream of a given blood sample. Thus, where multiple cell information of this type is desired, the standard commercial way of obtaining it is by preparing a microscope slide with the cells fixed on an image plane and having a human operator or pattern recognition machine count statistically significant numbers of the cells as the cells are observed one-at-a-time on the slide through a microscope.

Some attempts have been made in recent years to provide optical analysis of particles flowing in a flow stream. For instance, Kay, et al., *Journal of Histochemistry and Cytochemistry*, Volume 27, page 329 (1979) shows a Coulter type orifice for moving cells in single file with the cells magnified on a vidicon. Additionally, Kachel, et al., *Journal of Histochemistry and Cytochemistry*, Volume 27, page 335, shows a device for moving cells in single file through a microscopic area where they are photographed. While these workers have done some work in automating particle analysis in single file no successful work has been reported where automated particle analysis was accomplished in a flowing stream without the requirement of arranging the particles into a single file stream. See for instance *Flow Cytometry and Sorting* Melaned et al, John Wiley & Sons 1979, Chapter 1.

SUMMARY OF THE INVENTION

In accordance with this invention we have provided a method and apparatus for moving a fluid sample, preferably a blood sample, through a controlled flow path where the particles in the sample are confined to a shallow but broad imaging area which is on the order of the depth of the particles and many times wider than the particles. The stream of particles in the imaging area is magnified and a series of still frame images of the particles are prepared and then algebraically combined to generate measures of the cell content of the original flow stream. In this way more than one particle can be examined in a single field, and different particles can be optically distinguished with a number of important advantages. For instance, two cells flowing together can be optically recognized whereas a Coulter counter could recognize them as a single double-sized cell.

Preferably, the still frame images of the flow stream are provided by imaging the magnified image of the stream on a CCD (charge coupled device) camera from which still frame images are taken and analyzed in digital form. In this way the still frame images may be enhanced with the digital image enhancement techniques which have been developed for satellite pictures and the individual frames may be analyzed to provide data on individual cells, such as, size, cross-sectional area, shape, (circular cell, target cell, sickle cell, etc.), optical density, hemoglobin content on the cell basis, etc. Not only can individual cells be analyzed and optically sorted in this way, but additionally when the cells are so analyzed and sorted different types of cells may be individually counted to give automatically and at a single pass, the number of normal red cells per volume of sample, the number of target red cells per cc of sample, the number of sickled red cells per cc of sample, the number of white cells, the number of platelets, etc. per cc. of sample.

Thus, once a series of still frame images is prepared in digital form in accordance with this invention, a wide variety of very sophisticated information can be obtained about the particles in the series of images depending upon the complexity of computer equipment and software which may be used for analysis of the images.

Preferably information derived from still frame images is combined algebraically to provide composite information reflecting the content of the multiple still frame images and/or predetermined reference images, and the composite information thus obtained may be used in a variety of ways. Thus, in simple systems the information may be printed out, for instance, to advise a hematologist about composite measurements made from a blood sample. In more complex systems, the composite measurements may be used by process control, such as pressure in a homogenizer, temperature in a crystallizer, or nutrient feed rate in a microbial culture where the system monitors particle size or number.

Thus, it will be noted that the invention may be used for analysis of a variety of optically perceptible particles moving in a stream, both biological particles, such as cells in blood or cells, bacteria, casts and crystals in urine or particles in gas analyzers, etc., and the output of these measurements may be employed for process control, such as dispensing nutrients into a stream containing microorganisms as mentioned above, the control of the growth of polymers and crystals, etc.

The information which is provided may be correlated readily to the original volume of blood sample from which the still frame images are made by a variety of methods to calibrate the results for both particle size and concentration. For instance calibration may be accomplished by adding calibrator particles to the original blood sample in a known concentration so that the calibrator particles may be counted independently of the normal blood cells to provide volume calibration for the normal blood cells. Alternatively, calibration may be accomplished by providing a cross-hatch of fixed dimension in the field of view.

The flow stream of particles to be magnified and imaged is preferably provided in a flow chamber which moves the particles in a stream which is approximately the thickness of the thickest particles and many times wider than the widest particles, for instance, more than one hundred times as wide as the widest particles. The flow chamber might be designed to create turbulent flow to permit asymetric particles to be viewed from multiple directions. On the other hand the flow chamber may be designed to orient the particles.

Preferably the flow stream in the imaging area has a cross-sectional area of minimum shear which is not substantially larger than the minimum cross-sectional area of the particles whereby the particles are aligned in the flow stream with their minimum cross-sectional area extended transverse to their direction of flow. The term "minimum shear" is used herein to mean "minimum velocity gradient" so that a particle moving in the stream tends to align itself with the direction of the stream much as a log floating down a river will align itself with the direction of flow where there is a flow gradient.

DETAILED DESCRIPTION

These and other features of the invention will become apparent from the following description of a preferred apparatus practicing the invention in which:

FIG. 1 is a perspective view of apparatus for examining a flow stream in accordance with this invention.

FIG. 2 is a plan view of the flow chamber in FIG. 1.

FIG. 3 is a cross-sectional view of the apparatus of FIG. 2 taken on the plane indicated at 3—3.

FIG. 4 is a schematic diagram of the electronic processor employed by the apparatus of FIG. 1.

Referring now in detail to the drawings, and particularly to FIG. 1, the apparatus shown therein includes a body 10 containing a flow chamber having an inlet 12 for a blood sample and an outlet 14 with a passageway 16 extending between them past an imaging area 18. The passageway 16 has an inlet with a conduit 20 adapted to be connected to a volume of saline solution 22. As illustrated in FIGS. 2 and 3, the inlet 12 for the blood sample has a needle 24 in the passageway 16 downstream from the conduit 20 with the needle 24 connected to a container 26 adapted to hold the blood sample to be analyzed.

The cross-sectional area of the passageway 16 becomes progressively smaller as the passageway extends from the blood inlet 12 to the outlet 14 while at the same time the passageway 16 becomes much shallower and much wider. Thus, as illustrated in FIGS. 2 and 3 the passageway 16 has a width and depth of about 5,000 microns at the blood inlet 12 and a width and depth of about 500 microns at midpoint 28, and a depth of 100 microns with a width exceeding 5,000 microns at the examination area 18.

It will be appreciated that the flow stream through the examination area 18 is many times deeper than the largest cell which have a maximum dimension of about 20 microns, but with the flow passageway shaped in this way the blood stream entering through the opening 12 is confined to a stable flow path of minimum shear in the examination area 18, and the disc-like cells are oriented in that area with their maximum cross-sectional area visible in the plane of FIG. 2. The flow characteristics in the passageway 16 may be controlled by adjusting the fluid pressure in containers 22 and 26 either automatically or by adjusting the static heights thereof.

A microscope 30 is focused on the examination area 18 and the examination area 18 is illuminated from below by a strobe light 32 which is preferably a U.S. Scientific Instrument Corporation Model 3018 containing a 2UP1.5 lamp. The output of the microscope 30 is focused on a CCD camera 34 which is preferably a CCD camera model number TC1160BD manufactured by RCA. The output of the CCD camera is converted to a series of still frame images, and suitable electronic processors are employed for evaluating those images. One processor which may be employed is the processor marketed as Image Analysis System Model C-1285 by Hamamatsu Systems, Inc., Waltham, Mass. Preferably the output of the CCD camera is connected to an electronic processor 36 which is illustrated in greater detail in FIG. 4 and includes a black and white television monitor 38 and a frame grabber 40 which stores still frame images of the subject viewed by the CCD camera. The frame grabber is preferably a Model FG08 frame grabber made by the Matrox Corporation of Montreal, the output of which is supplied to a video refresh memory 42 Model RGB 256 made by Matrox Corporation which are both coupled to the multibus 44 of the central processing unit 46 which is preferably an Intel 80/20 computer. The multibus is also coupled to a 48K random access memory 48 of Electronic Solutions, Inc., and a 16K dual port random access memory 50 Model RM 117 of Data Cube Corporation. The output of the video refresh memory is also coupled to a color monitor 52 which may be used to provide digitally enhanced video images of individual still frames for human examination.

The second output of the dual port ram 50 is connected to a multibus 54 which is connected to an Applied Micro Devices central processing unit 56, a 48K random access memory of Electronic Solutions, Inc. 58 and removable storage in the form of a floppy disc controller 60, such as an Advanced Micro Devices Model 8/8 and two units of Shugart floppy disc storage 62.

A wide variety of programming may be employed for processing pictures with the apparatus of FIG. 4 depending upon the particular task which user wishes to perform.

As mentioned above, the programming of the Hamamatsu System 1285 may be employed. Preferably, however, the programming is performed as follows:

The tasks are first divided into those which must address each pixel in a given image and those which only address a small subset of the total. Since much time will be spent in the first class of tasks, they are programmed in assembly language on the interface processor 46 (the Intel 80/20 in FIG. 4). The output of these operations are then transferred to the host machine 56 via the dual ported ram 50. On the host side almost all of the necessary programming is more suitably done in a high level language such as Pascal (BASIC or FORTRAN could be in principal be used also). The types of tasks that are done in the assembly language includes greyscale transformations, convolutions, and greyscale histogram calculations. The types of tasks done on the host side include overall control of the other devices, identification and segmentation of object of interest in the field of view, calculation of parameters associated with objects thus found, and formating the output of results. Another way of considering this separation of tasks in this fashion is that tasks which must be performed at speeds great compared to a human operator are done in assembly. Tasks which are either complicated or which can operate at less than the maximum speed can be programmed in the higher language. Objects are found in a field of view primarily by setting a greyscale window function for values known to be characteristic of the desired object. These values can be established by prior knowledge or by well-known histogram techniques. When a pixel belonging to an object has been located in the field of view, an edge tracing program is invoked to outline the whole object associated with that pixel. Once the edge has been found, then many relevant parameters such as location, area, integrated optical density, and various moments can easily be calculated. Probability of membership in previously defined subgroups can be determined from these derived parameters by means of standard decision theory.

Definitions of blood cell morphoplogy classifications are established by trained observers. These definitions are then used as the basis of the selected algorithms. Accuracy of the method is determined by comparison of machine results with those of trained observers examining the same samples. Output of the results can be programmed to be any of a variety of formats. Histograms, line plots, and tabular summaries are available for particular needs.

What is claimed is:

1. Apparatus for analysis of particles in a fluid which comprises
   a flow chamber having an inlet and an outlet and shaped to convey fluid from the inlet to the outlet with particles in the fluid suspended in a path, a portion of said path having a width substantially greater than its thickness;
   said path shaped to convey said fluid such that said particles are aligned in the flow stream substantially with their minimum cross-sectional area extended transverse to their direction of flow and their maximum cross-sectional area extended substantially parallel to said width;
   microscopic means adapted to be focused on the path including an area of the path substantially greater than the area of the largest of the particles, and
   image pick-up means for picking up substantially still frame images of particles in the path through the microscopic means.

2. The apparatus of claim 1 characterized further by the inclusion of processor means connected to the image pick-up means for analyzing the still frame images.

3. The apparatus of claim 2 characterized further by the inclusion of controller means coupled to the processor means for altering the condition of the fluid in response to analysis by the processor.

4. Apparatus for analysis of predetermined particles in a liquid which comprises
   a flow chamber having an inlet and an outlet and shaped to convey liquid from the inlet to the outlet with particles in the liquid suspended in a path, a portion of said path having a width at least ten times it thickness,
   shear force distributing means for conveying said fluid such that said particles are aligned in the flow stream substantially with their minimum cross-sectional area extended transverse to their direction of flow and their maximum cross-sectional area extended substantially parallel to said width,
   microscopic means adapted to be focused on the path including an area of the path at least one hundred times the area of the largest particles,
   image pick-up means for picking up substantially still frame images of particles in the path through the microscopic means with the image pick-up means including means for storing at least one of the still frame images at a time in digital form, and
   processor means connected to the image pick-up means for algebraically combining selected components of the recorded still frame images to generate algebraic sums representing the particles in multiple images.

5. The apparatus of claim 4 in which the flow chamber has supply means for supplying an envelope of fluid around the inlet and moving from the inlet to the outlet whereby the path for the particles is surrounded by the envelope of fluid.

6. The apparatus of claim 5 characterized further in that said apparatus contains a volume of liquid as said envelope of focusing fluid and sample cells as the predetermined particles.

7. The apparatus of claim 1 or 4 in which said flow chamber comprises
   a passageway extending from the inlet to the outlet with the passageway having an imaging area thereof on which said microscopic means is focused,
   the passageway having a cross-sectional area which decreases substantially as the passageway extends from the inlet to the imaging area, a thickness which decreases substantially as the passageway moves from the inlet to the imaging area, and a width which decreases from the inlet and then increases substantially as the passageway moves to the imaging area.

8. The method of analyzing particles in a fluid which comprises
   having a predetermined direction of motion while distributing the fluid sample over an extended area having a width and a thickness both measured perpendicular to the direction of flow, with the width many times the thickness, such that said particles are aligned in the direction of motion substantially with their minimum cross-sectional area extended transverse to the direction of motion and their maximum cross-sectional area extended substantially parallel to said width,
   forming a series of still frame images of the fluid sample at a predetermined location in the flow path viewed in a direction parallel to the thickness, and
   algebraically combining the number of particles located and their characteristics.

9. The method of claim 8 characterized further in that the fluid is a biological sample.

10. The method of claim 8 characterized further by the inclusion of the step of altering a condition of the fluid in response to the algebraic combination.

11. The method of claim 8 wherein said particles are asymmetrically shaped.

12. The method of claim 9 wherein said sample contains blood cells.

13. The method of claim 12 wherein said sample is blood.

14. The method of claim 12 wherein said sample is urine.

15. A flow chamber for analysis of fluid containing particles flowing therethrough said chamber comprising:
    an inlet;
    an outlet;
    a path for said fluid flowing from said inlet to said outlet;
    said path having a portion adapted for viewing with said portion having a width substantially greater than its thickness and an area substantially greater than the area of the largest of the particles;
    said path having a cross-sectional area which decreases substantially as said path extends from the inlet to said portion, a thickness which decreases substantially as said path moves from the inlet to said portion, and a width which decreases from the inlet then increases substantially as said path moves to said portion.

16. The chamber of claim 15 wherein said fluid is a biological sample.

* * * * *